(12) United States Patent
Boss et al.

(10) Patent No.: US 8,805,756 B2
(45) Date of Patent: Aug. 12, 2014

(54) ENHANCED DEEPQA IN A MEDICAL ENVIRONMENT

(71) Applicants: Gregory J. Boss, Saginaw, MI (US); Ching-Hua Chen-Ritzo, New York, NY (US); Rick A. Hamilton, II, Charlottesville, VA (US); Jianying Hu, Bronx, NY (US); Clifford A. Pickover, Yorktown Heights, NY (US)

(72) Inventors: Gregory J. Boss, Saginaw, MI (US); Ching-Hua Chen-Ritzo, New York, NY (US); Rick A. Hamilton, II, Charlottesville, VA (US); Jianying Hu, Bronx, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/067,416

(22) Filed: Oct. 30, 2013

(65) Prior Publication Data

US 2014/0058986 A1    Feb. 27, 2014

Related U.S. Application Data

(63) Continuation of application No. 13/302,120, filed on Nov. 22, 2011.

(51) Int. Cl.
*G06F 15/18* (2006.01)
*G06N 5/00* (2006.01)
*G06K 9/62* (2006.01)

(52) U.S. Cl.
CPC ... *G06N 5/00* (2013.01); *G06K 9/62* (2013.01)
USPC .......................................................... 706/12

(58) Field of Classification Search
CPC .................................. G06N 5/00; G06K 9/62
See application file for complete search history.

(56) References Cited

U.S. PATENT DOCUMENTS

| 7,873,624 | B2 | 1/2011 | Agichtein et al. |
| 2004/0068454 | A1 | 4/2004 | Jacobus |
| 2008/0140786 | A1 | 6/2008 | Tran |
| 2011/0151898 | A1 | 6/2011 | Chandra et al. |
| 2011/0153517 | A1 | 6/2011 | Thomas |

FOREIGN PATENT DOCUMENTS

| WO | WO2009021198 | 4/2009 |
| WO | WO2010045614 | 4/2010 |
| WO | WO2011042594 | 4/2011 |

OTHER PUBLICATIONS

USPTO; Examination Correspondence from a Related Patent Application(Office Action 1 Reply), U.S. Appl. No. 13/302,120, filed Nov. 15, 2011 by Gregory J. Boss.

(Continued)

*Primary Examiner* — Alan Chen
(74) *Attorney, Agent, or Firm* — Robert H. Frantz; David A. Mims, Jr.; Damion C. Josephs

(57) ABSTRACT

A DeepQA engine is enhanced to provide a digital medical investigation tool which assists a medical professional in researching potential causes of a set of patient conditions, including clues, facts and factoids about the patient. The DeepQA engine provides one or more answers to a natural language question with confidence levels for each answer. If a confidence level falls below a threshold, the enhanced DeepQA engine performs a crowd sourcing operation to gather additional information from one or more domain experts. The domain expert responses are provided to the medical professional, and are learned by the enhanced DeepQA system to provide for better research of similar patient conditions in future queries.

20 Claims, 4 Drawing Sheets

(56) References Cited

OTHER PUBLICATIONS

NPL; Examination Correspondence from a Related U.S. Appl. No. 13/302,120, filed Nov. 22, 2011 by Gregory J. Boss.

IBM; "High Throughout Computing on IBM's Blue Gene"; retrieved on Sep. 13, 2011 from http://www-03.ibm.com/systems/resources/HTC_WhitePaper_V2_050508.pdf.

IBM; "IBM System Blue Gene/p Solution";retrieved on Sep. 13, 2011 from http://www-03.ibm.com/systems/resources/bgpspecsheet4.pdf.

IBM; "DeepQA" retrieved on Sep. 13, 2011 from http://www.research.ibm.com/deepqa/faq.shtml.

IBM; "IBM System Blue Gene Solution:Blue Gene/P Application Development"; retrieved on Sep. 14, 2011 from http://www.redbooks.ibm.com/redbooks/pdfs/sg247287.pdf.

Ferrucci, David, et al; "Building Watson: An Overview of the DeepQA Project", AI Magazine, Fall 2010, pp. 59-79, retrieved on Nov. 11, 2011 from http://www.stanford.edu/class/cs124/AIMagzine-DeepQA.pdf.

USPTO; Examination Correspondence from a Related U.S. Appl. No. 13/302,120, filed Nov. 22, 2011 by Gregory Jensen Boss.

ENHANCED DEEPQA IN A MEDICAL ENVIRONMENT

CROSS-REFERENCE TO RELATED APPLICATIONS (CLAIMING BENEFIT UNDER 35 U.S.C. 120)

This is a continuation application of U.S. patent application Ser. No. 13/302,120, filed on Nov. 22, 2011, by Gregory J. Boss, et al.

FEDERALLY SPONSORED RESEARCH AND DEVELOPMENT STATEMENT

None.

MICROFICHE APPENDIX

Not applicable.

INCORPORATION BY REFERENCE

Related U.S. patent application Ser. No. 13/302,120, filed on Nov. 22, 2011, by Gregory J. Boss, et al., is incorporated by reference in its entirety including drawings.

FIELD OF THE INVENTION

The invention generally relates to automated crowd sourcing enhancements to deep question-answer architecture systems, including combinations of Natural Language Processing, Information Retrieval, Knowledge Representation and Reasoning, and Machine Learning technologies, and the field of open-domain question answering. The invention more particularly relates to such crowd sourcing enhancements in the fields of medicine and health care.

BACKGROUND OF INVENTION

International Business Machines Corporation (IBM) has published details of computing methods and technologies that are able to assist humans with certain types of semantic query and search operations, such as the type of natural question-and-answer paradigm of a medical environment. IBM researchers scientists have been working on Deep Question-Answering (DeepQA) methods that are able to understand complex questions posed (and input) in natural language, and are able to answer the question with enough precision, confidence, and speed to augment human handling of the same questions within a given environment, such as a medical inquiry and diagnostic paradigm where time-to-answer is of the essence.

DeepQA is an application of advanced Natural Language Processing, Information Retrieval, Knowledge Representation and Reasoning, and Machine Learning technologies to the field of open-domain question answering, all executing on a suitable computing platform. Such methods of hypothesis generation, evidence gathering, analysis, and scoring may be effectively executed by a wide range of computing platforms.

Similarly, IBM has also published computing methods which combine semantic elements with information search elements to form Unstructured Information Management Architecture (UIMA), which is now maintained as an open source project by the Apache organization.

Whereas ample information is available in the public domain regarding DeepQA and UIMA, the present disclosure presumes those ordinarily skilled in the art may access and apply that information to realized embodiments of the following invention.

There is a need in the art to provide information to medical professionals based upon clues, facts, and unanswered questions in order to assist in proper diagnoses by those professionals in a timely manner. The increasing number of known diseases, syndromes, drug side effects, drug interactions and possibly rapid spread of contagions as a result of rapid movement of people and cargo throughout the world has created mass volumes of information which may be unwieldy to utilize when there is time pressure to make a medical decision.

While only a qualified medical professional may make an actual diagnosis using human judgment and intuition, timely and cost effective research tools are needed to assist these medical professionals as accurately and quickly as possible.

SUMMARY OF THE INVENTION

A DeepQA engine is enhanced to provide a digital medical investigation tool which assists a medical professional in researching potential causes of a set of patient conditions, including clues, facts and factoids about the patient. The DeepQA engine provides one or more answers to a natural language question with confidence levels for each answer. If a confidence level falls below a threshold the enhanced DeepQA engine automatically performs a crowd sourcing operation to gather additional information from one or more domain experts. The domain expert responses are provided to the medical professional in an automatic fashion, and are learned by the enhanced DeepQA system to provide for better research of similar patient conditions in future queries.

BRIEF DESCRIPTION OF THE DRAWINGS

The description set forth herein is illustrated by the several drawings.

DETAILED DESCRIPTION OF EMBODIMENT(S) OF THE INVENTION

Figure 1:
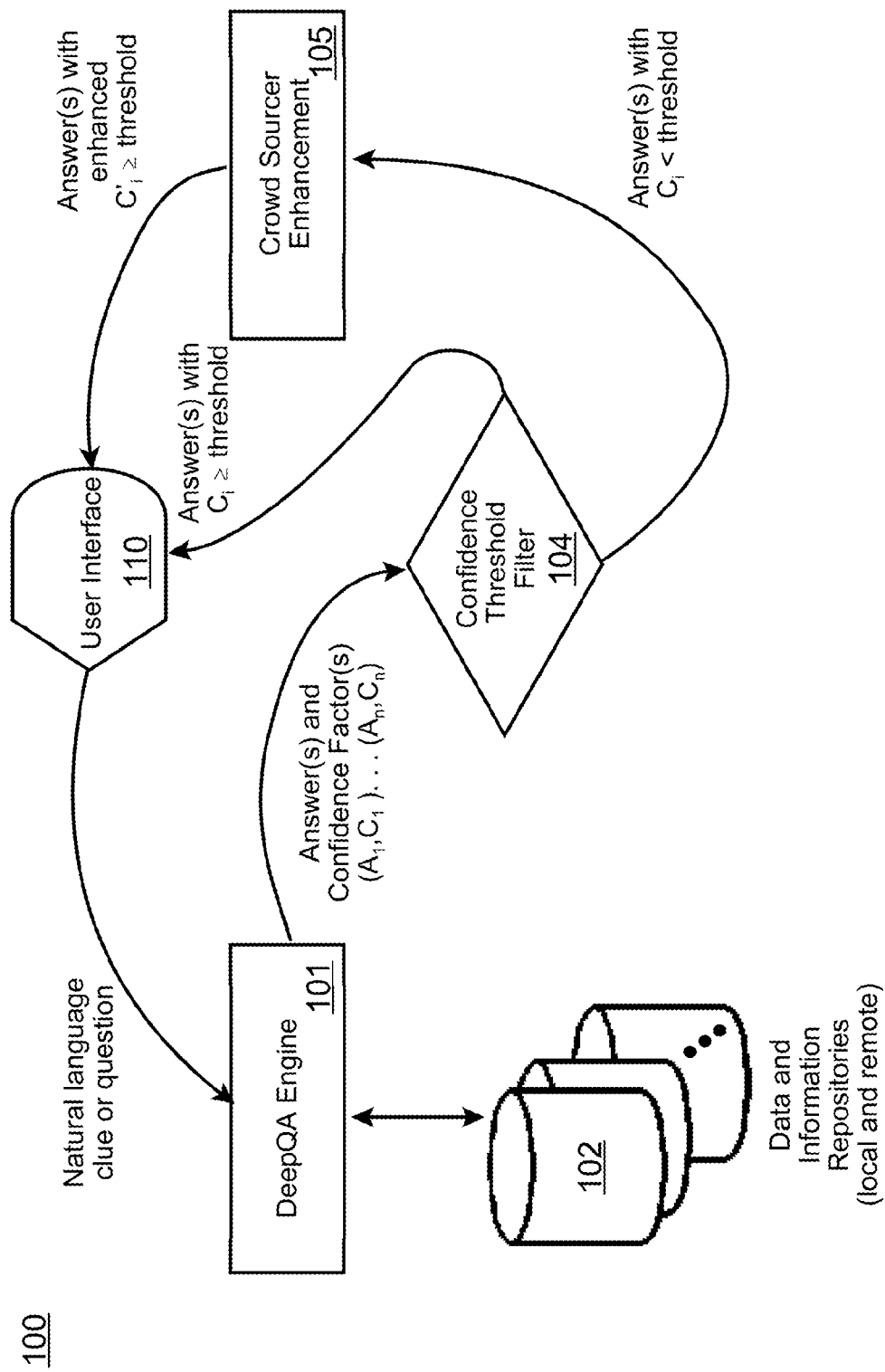
FIG. 1 shows the functional relationship between the crowd sourcer enhancement, a confidence level filter, and the Deep QA system.

The inventors of the present and related inventions have recognized and anticipated problems not yet recognized by those skilled in the relevant arts. The inventors have realized that the paradigm presented by medical and health care industries to quickly find and evaluate possible medical conditions based on questions, clues, facts and factoids about a particular patient's condition(s) or group of patients conditions is not well satisfied by traditional web search engines. When presented with a new set of health conditions about a patient, for example, such as the patient's age, known health issues, vital signs, complaints, etc., all of which are "clues, facts and factoids" to a problem to be solved, the doctor or health care professional must deduce what the problem is—e.g., what one or more medical causes may be to blame for the patient's condition. When the health care professional uses a web search engine to retrieve information using key words, he or she may receive thousands of return documents, relevancy-ranked, which may or may not contain reliable information. Further, the health care professional must dig into those documents to determine better key words to use in a revised search, and to actually infer a possible root cause of the patient's condition (e.g. diagnose the patient). The present inventors have realized that DeepQA computing techniques, coupled with crowd sourcing of domain experts on demand, can greatly benefit such a health care professional in this information research effort, thereby allowing the health care professional to more quickly diagnose the patient based upon a greater amount of information and data.

Embodiments according to the present invention provide an enhancement to deep question-answer (DeepQA) information handling computing systems, i.e., those computing systems which answer natural language questions by querying data repositories and applying elements of language processing, information retrieval, and machine learning to arrive at a conclusion.

More particularly, embodiments according to this invention provide information researching tools for enhancing such responses, including the use of queries to human experts under various circumstances (e.g. expert crowd sourcing), so that the presented answer or answers have higher value, accuracy, and trustworthiness than answers which may be produced by a simple repository query such as a web search engine alone. These enhancements are accomplished using components which are automatically triggered based on criteria, which will be described in more detail in the following paragraphs.

Disclosed is a method for enhancing DeepQA (deep question and answering) processing methods by automatically triggering expert crowd-sourcing when a confidence level associated with an answer is below a threshold. In this manner, an inquiring user is more likely to obtain valuable, reliable, and trustworthy information for performing a task such as diagnosing a medical patient. Various conditions exist around such crowd-sourcing decisions, which are also included in details below.

For the purposes of this disclosure, "diagnosis" will refer to an action performed by a suitably-qualified medical professional person, not by a computer. Embodiments of the present invention provide quicker and more thorough research to suitably-qualified medical professional persons in response to the inquiring user's natural language inputs of questions, clues, facts and factoids. The inquiring person may be the suitably-qualified medical professional person, or may be an assistant, such as a nurse or Emergency Medical Technician. The results of the DeepQA process are not, in and of themselves, an diagnosis of a medical condition, per se, but instead are relevant information resources for a human to make such a diagnosis.

Also for the purposes of this disclosure, the terms "clue", "fact" and "factiod" shall mean a bit of information available which may or may not be relevant to the actual root-cause of the medical condition which will eventually be diagnosed by the medical professional. For example, an unresponsive patient is presented at an emergency room. Facts would include bits of information that are measurable and verifiable, such as the patient's temperature, blood pressure, age, gender, pupil responsiveness, skin pallor, and known medical conditions (diabetes, stroke, epilepsy, cancer, etc.). Factoids would include information items which may or may not be relevant or true, but must be considered with some weight in the diagnosing process, such as the patient might have been stung by a bee during a visit to a farm earlier in the day, and might be allergic to bee stings, but none of this is known for sure. Clues would include other information items that might be useful in narrowing possible diagnoses, such as it is known that influenza is spreading at the present time in the general area, or that the patient recently started taking a new prescription drug. These clues, facts and factoids may be collected from a number of sources, such as EMT's, nurses, relatives, co-workers, police officers, news organizations, epidemiology centers, poison centers, etc. These general categories of information are intended to refer to diagnostic observations and data collections, such as those described in International Classification of Diseases, Ninth Revision, Clinical Modification (ICD-9-CM) promulgated in the United States by the Centers for Disease Control and Prevention (CDC). The ICD-9-CM refers to many patient conditions as "probable," "suspected," "likely," "questionable," "possible," or "rule out". In other countries and jurisdictions, other codes and terms may be used, so the terms facts, factoids and clues are used to refer to information in all of these contexts and standardization paradigms. For the purposes of this disclosure, any information which may be relevant to affirmative decision making in determining possible causes, explanations, solutions or answers to the posed question, or for elimination of possible causes, explanations, solutions or answers to the posed question will be referred to as facts, factoids or clues.

Also for the purposes of the present disclosure, an "inquiring user" will refer to human user who is using or operating the embodiment of the invention to perform the research necessary to enhance a medical professional's ability to quickly and accurately diagnose the patient. An "expert user" will refer to a domain expert who may be contacted via an embodiment of the invention to obtain ideas, suggestions, information, data or recommendations, such as a radiologist, poison control specialist, hematologist, endocrinologist, etc.

Further, for the purposes of this disclosure, "missing information" will refer to clues, facts, and factoids which are not presently provided to the invention but which have been typically been included with previous similar requests. "Supplemental information" or "additional information" will refer to clues, facts, and factoids which the initial research (or a previous pass of research) indicates would be pivotal or useful in distinguishing one line of inquiry from another line of inquiry in the research.

FIG. 1 illustrates an example in the medical and healthcare domain, consider application of such DeepQA technologies as a "Digital Medical Investigator," (DMI) to show how higher confidence answers may be derived using this technique. An inquiring user (e.g. a doctor, physician, patient, nurse, EMT or third party) through a first user interface (110) may ask a question in natural language, not expressed in a specialized query syntax, of the computing system containing the words "multiplesclerosis," "fever," and "skin rash", such as:

"what might cause a 52-year old male with multiple sclerosis to have a fever and skin rash?"

Next, the DMI's DeepQA (101) process, after performing it's logical processes for search and analysis, suggests one or more possible answers with confidences for each answer, based upon a combination of several of the following elements, as shown in FIG. 1:

(a) An analysis of information in databases (102);
(b) A crowd-sourcing element (105), extending upon the DeepQA capabilities, which is automatically triggered when one or more diagnoses (e.g. answer) confidence level is low (104);
(c) An analysis of past inquiring user queries, along with an inquiring user profile that specifies information about the inquiring user;
(d) An analysis of word combinations used for similar inquiring users (not shown);
(e) optionally, a learning step in which an analysis of prior diagnosis including a feedback loop from the inquiring user indicating if the answer was considered to have been "correct"; and
(f) an expert user rating system and analysis of the feedback loop in (e) that could be incorporated into already existing auto-tuning technologies already realized in DeepQA systems.

Note that in (e), for example, after supplying an answer, potentially tagged as "low confidence", the inquiring user may indicate the correct answer if the DMI-supplied response was found to be incorrect. The inventors note this tagging itself can have a confidence level associated with it. For example, a physician may be certain with "very high" or simply "high" confidence that an answer is either correct or incorrect, and thus this degree of confidence can be used to weigh such kinds of feedback.

Methods to Increase Response Confidence Level by Querying the Subject on Missing Information or by Obtaining Material about the Subject.

Figure 2:
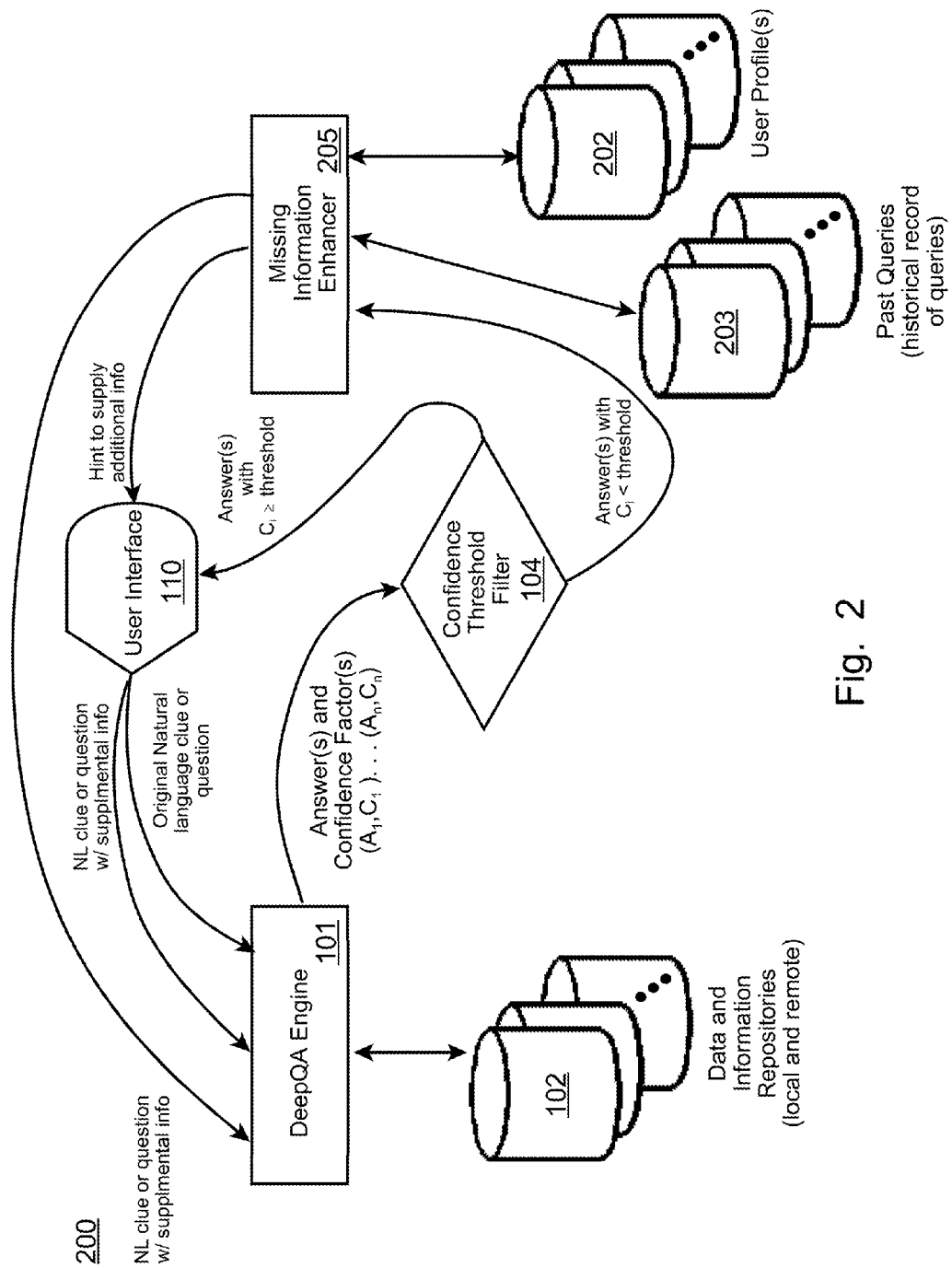
FIG. 2 illustrates more details of the generalized functional relationship of FIG. 1 including new functional components to determine and supplement information which is likely missing from the original question or clue.

In one optional functional feature (205) of embodiments according to the present invention illustrated in FIG. 2, the DMI (200) may make use of a patient profile (202), stored by a computing device, which specifies various patient attributes including comprehensive medical records, or some subset of attributes such as previous diagnoses and disease state (e.g. advanced vs. mild), user nationality, language, or occupation, and other such patient-specific information. This profile may be queried to aid the system in providing a relevant and/or higher-confidence answer.

Using this information, the DMI system may help the inquiring user frame his or her natural language questions to optimize the value or accuracy of the returned answer by providing hints or suggestions to the inquiring user for additional information via the user interface (110). Optionally, the DMI may prompt the inquiring user for key missing data, such as the list of vital signs was missing the patient's blood pressure and with this reading, confidence levels could increase from 30% to 60%. This value may be requested accordingly. Note that the DMI system may learn what information to prompt for based on past histories (203). According to the present enhancement to DeepQA systems and methods, the existing DeepQA systems also determine definitively why the confidence score is low. Embodiments of the present enhancement will use the known factors causing low confidence to optionally trigger patient response method, crowd sourcing, or both, so as to increase the confidence level. The system may know, for example, that the combination of 3 missing pieces of information related to (health history 20%, current blood pressure 15%, and perhaps genetic lineage 10%) may increase the confidence level by 45%. In this scenario it would be advantageous to first ask the questions that will affect the confidence levels the most.

For example, if 99% of the time, a inquiring user supplied a blood pressure vital sign value when performing a query about strokes, the DMI system may suggest this fact be supplied when another inquiring user performs a query about a possible stroke.

This may result in one or both of (a) a natural language question with supplemental information being submitted from the first user interface (11) to the DeepQA engine (101), and (b) directly from the information enhancer (205) to the DeepQA engine (101).

Method to Increase Response Confidence Level by Querying Subject Matter Expert Users.

Figure 3:
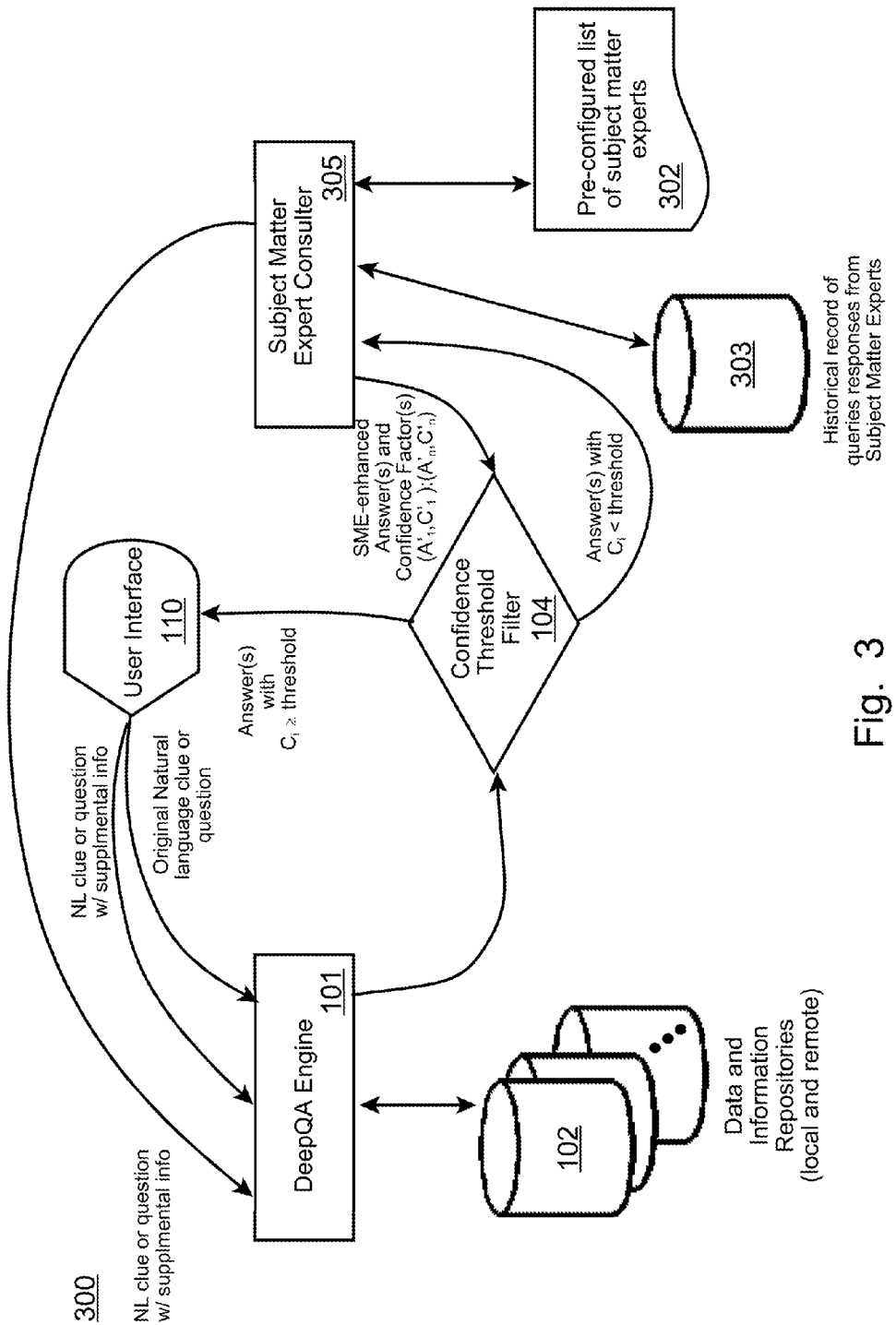
FIG. 3 depicts more details of the generalized functional relationship of FIG. 1 including new functional components to consult subject matter experts in order to further raise the confidence level of potential answers by supplementing the answer, enhancing the question, or both.

According to another available functional feature of enhanced embodiments of the DMI as shown (300) in FIG. 3, for instances where sufficient time is available to complete an analysis, but sufficient information is not available for the analysis to reach a criterion confidence threshold, an active learning component (305) is triggered which summarizes the situation and context and distributes this information electronically to a pre-configured set of expert users, such as domain expertise advisors (medical specialists, drug interaction specialists, pharmacists, etc.), family-members, and caregivers (302). Contact and interface to these domain expert users may be through a second user interface such as an email system, a short message text (SMS) texting system, a web portal, a voice response unit, a voice messaging system, and an auto-dialer for voice telephone calls. Their responses are then incorporated (303) into the DMI system's analysis data for future use, such as by modifying the answers and confidence factors and re-evaluating (104) them against the confidence threshold, or submitting an enhanced clue or question to the DeepQA engine (101) incorporating additional information gathered from the subject matter experts, or a combination of both.

Method to Delay a Response Until a Confidence Level Threshold is Achieved.

Confidence values, for example, may grow as crowdsourcing is performed, and during this time may approach some threshold. At this point, the action-taking component is allowed to take action and prompt the user, provide a response to the user, or a combination of both. Note that the confidence level can be indicated, e.g. by a visual indicator, audio indicator, textual change, speech change, e.g. louder if more confident or switching to a different voice when more confident. This delay can be visualized by tracing the various feedback paths shown in FIGS. 1, 2 and 3, which lead back into the DeepQA engine or back to the threshold filter.

Logical Processes.

Logical processes according to the present invention can be seen from the foregoing diagrams and descriptions. For greater understanding of the logical processes, and optional embodiment features, the follow paragraphs provide both general and more detailed descriptions of the various components of embodiments of the invention.

Regarding the particular application of methods of the invention to the medical and healthcare fields, generally speaking, embodiments will include a first phase such as:
1. Inputs are made by an inquiring user to the DMI system concerning potential causes of medical symptoms and conditions of a patient, where the symptoms and conditions may include clues, facts and factoids as available to the inquiring user.
2. The DMI system analyzes the inputs (textual or otherwise) and attempts to provide one or more useful answers, optionally with a confidence factor for each answer, via established DeepQA techniques.

3. If a confidence level of an answer is below a threshold, the DMI system may perform one or more of the following steps:
   a. Trigger expert-user crowd-sourcing as described in the foregoing paragraphs.
   b. Prompt the inquiring user through additional question(s) to obtain missing information, supplemental information, or both, in order to increase the confidence of an answer, wherein the prompts for missing or supplemental information are determined from an analysis of past inquiring user queries.
   c. Analyze the patient's responses for indications of "confidence" (i.e. customary biometric techniques) to detect variations in stress levels, e.g. if the patient's voice and/or heart rate indicate an exaggeration/inaccuracy with respect to "true" information, that element could be scaled down (weighted less) in comparison to other described symptoms.
   d. When confidence is above a threshold, the DMI system conveys the answer (diagnosis) to the inquiring user.

A second phase may be conducted using a machine learning mechanism to perform a pervasive confidence estimate. The DMI system ultimately produces a ranked list of answers (i.e. of possible responses to provide the user), each with a confidence value (to decide whether or not to "risk" making a response in a particular situation) and associated with a collection of supporting evidence. If the confidence value is above a threshold, then the system conveys the answer to the user. An Unstructured Information Management Architecture (UIMA) may be used to facilitate the Natural Language Processing (NLP).

Also in the second phase, the inquiring user could specify the desired confidence level, and additionally, provide the price that he or she is willing to pay for an answer with that level of confidence. More generally, this specification of price and confidence level could be continuous or tiered.

Regarding crowd sourcing in a third phase, the DMI system identifies eligible expert users (e.g., members of the 'crowd') with respect to the inquiring user's question. The DMI system ranks the expert users in the crowd in order of the probable magnitude of each of the expert user's contributed answer towards increasing the confidence level of the DMI system's answer. The ranking may be determined by analyzing the quality of past contributions from each expert user on similar questions or by analyzing the feedback ranking of prior expert user contributions derived from specific crowd sourced subject matter expert users.

Also, in the third phase, the crowd sourcing element may implement a process for setting the price for solicited information, as well as setting a start time and deadline for soliciting and receiving information, respectively, from ranked experts. After the deadline is reached, the price could be adjusted and the deadline extended, or the offer could be withdrawn. These decisions could be based on the information collected during the crowd-sourcing effort, or through other efforts. They could also be based on the desired confidence level and the price the user is willing to pay for a given confidence level—see elaboration of the fourth phase, below. The effect of implementing this process is that it could improve the efficiency (i.e., cost and speed to reach certain confidence level) with which information is collected from ranked experts.

The precise embodiment and logical flow of embodiments of this invention may be described in several ways. Another set of sample steps may be outlined below:

(1) DeepQA system is queried with natural language problem statement, per the publicly disclosed DeepQA methods.

(2) DeepQA system returns tentative set of possible answers, per the publicly disclosed DeepQA methods.

(3) In novel enhancements, if the answer(s) fall below a certain confidence level, which may be statically or dynamically determined, then query is made to the inquiring user, and optionally to one or more expert users:

Tentative answers may or may not be presented to question initiator at this time. A holding time may be set by the user or third-party. For example, the user may say that he/she is willing to wait 3 minutes for an answer, in order to reach a higher confidence level. During this time, the user does not need to have a response.

Query may be made using a variety of selection techniques, including:
  i. using a general predetermined and prepopulated list;
  ii. using dynamically discovered or predetermined known experts in germane fields, e.g., authors of papers or holders of patents;
  iii. consulting persons with known circumstances similar to that of question initiator, e.g., via medical diagnoses, occupation, or expertise;
  iv. consulting persons with known circumstances similar to that indicated by tentative responses, e.g., medical diagnoses, occupation, or expertise.

(4) Answers may be determined back to question initiator in a variety of ways, including one or more of the following:
  i. providing to the inquiring user full text of responses;
  ii. providing to the inquiring user the originally derived responses, augmented by relevant text from human respondents;
  iii. providing to the inquiring user only the augmented answers, where voting by the expert users could be integrated into the system-derived response, along with a new confidence level to be presented to the question initiator.

Please note that in the foregoing paragraphs, where "consult with" certain expert users is stated, it is meant that messages, such as text messages, emails, or automated voice response calls, are initiated to technological devices known to be associated with the users for consultation, such as their telephones, their computers, their messaging client devices and accounts (e.g. Instant Messenger, Twitter™), their electronic mail accounts, their personal social accounts (FaceBook™, Google+™), and their professional social accounts (e.g. LinkedIn™, Spoke™). Please also note that references to providing the user (e.g. the questioner) with information or gathering information from an expert user also is meant that messages, screens, prompts, dialogs, audible messages, indicators, icons, and other means of user interface technology may be employed on the user interface portions (display, screen, keyboard, pointer, etc.) of the same types of devices (telephones, email accounts and devices, messaging client accounts and devices, social accounts, etc.).

The inquiring user may, in some embodiments, obtain a report as to how the response was determined. The report may be simple, such as indicators regarding databases used, crowd-sourcing used, possible remuneration for such use, etc. Optionally, the report may contain more information.

System and Method to Dispense Time-Variable Drug Prescriptions.

The aforementioned DeepQA system may have an optional element that is tailored to the needs of drug prescribers and patients who require drugs. More particularly, this component involves a drug prescription that can change over time, even after it has been dispensed to the patient. The following is an example based on the scenario above where the DMI system makes an initial assessment with help from the existing DeepQA engine. However, assume that in this example, two hours after the initial answer from the DMI system the DeepQA continues after analyzing the additional data from crowd sourcing, scanning additional data sources and other doctors, domain experts (family members, caregivers), and the system updates its recommendation. The doctor sees the updated recommendation or research results and needs to change the prescription for the patient who has already left the office. In today's world, the physician cannot change the prescription even if the patient hasn't filled the prescription at the pharmacy yet without calling the pharmacy directly.

This new method involves placing a bar code or UNID on each prescription associated with a centralized prescription data repository. When the pharmacist goes to fill the prescription, they enter in or scan the prescription's code, the DMI system queries the repository for the latest prescription, and the modified or updated prescription is filled, not the original one.

Appropriate security elements are preferably provided so to respect patient privacy or misuse of the system. Moreover, optionally, this invention may use an indicator associated with the packaging of a drug, e.g. an LED affixed to a bottle of pills. This indicator may change status (e.g. color, blink, etc.) if some change has been made to the prescription after the pharmacist has filled it. This indication may be of value to any of: the pharmacist, the patient, store personnel, a caregiver.

The following points are ancillary to the primary novelty, but may be used to help establish context and provide other embodiment details, should this disclosure move forward for IP protection. In its operation, the DP may collect data using a variety of techniques including text input from speech recognition, keyboards, mobile phones, etc. Such inputs may be made synchronously, i.e., in real time, or through asynchronous means, e.g., batch importation. Note further that this invention need not be restricted to typical inputs such as a user's voice, but it can also have application for people with impaired voices or motor disorders, e.g. through brain wave analysis, muscle twitches, etc. For example, if a motor-disabled person is grasping for a word, and a brain wave analysis and facial tic analysis suggests a certain likely word, this information may be applied to the selection of a suggested word.

Suitable Computing Platform.

Regarding computers for executing the logical processes set forth herein, it will be readily recognized by those skilled in the art that a variety of computers are suitable and will become suitable as memory, processing, and communications capacities of computers and portable devices increases. In such embodiments, the operative invention includes the combination of the programmable computing platform and the programs together. In other embodiments, some or all of the logical processes may be committed to dedicated or specialized electronic circuitry, such as Application Specific Integrated Circuits or programmable logic devices.

Figure 4:
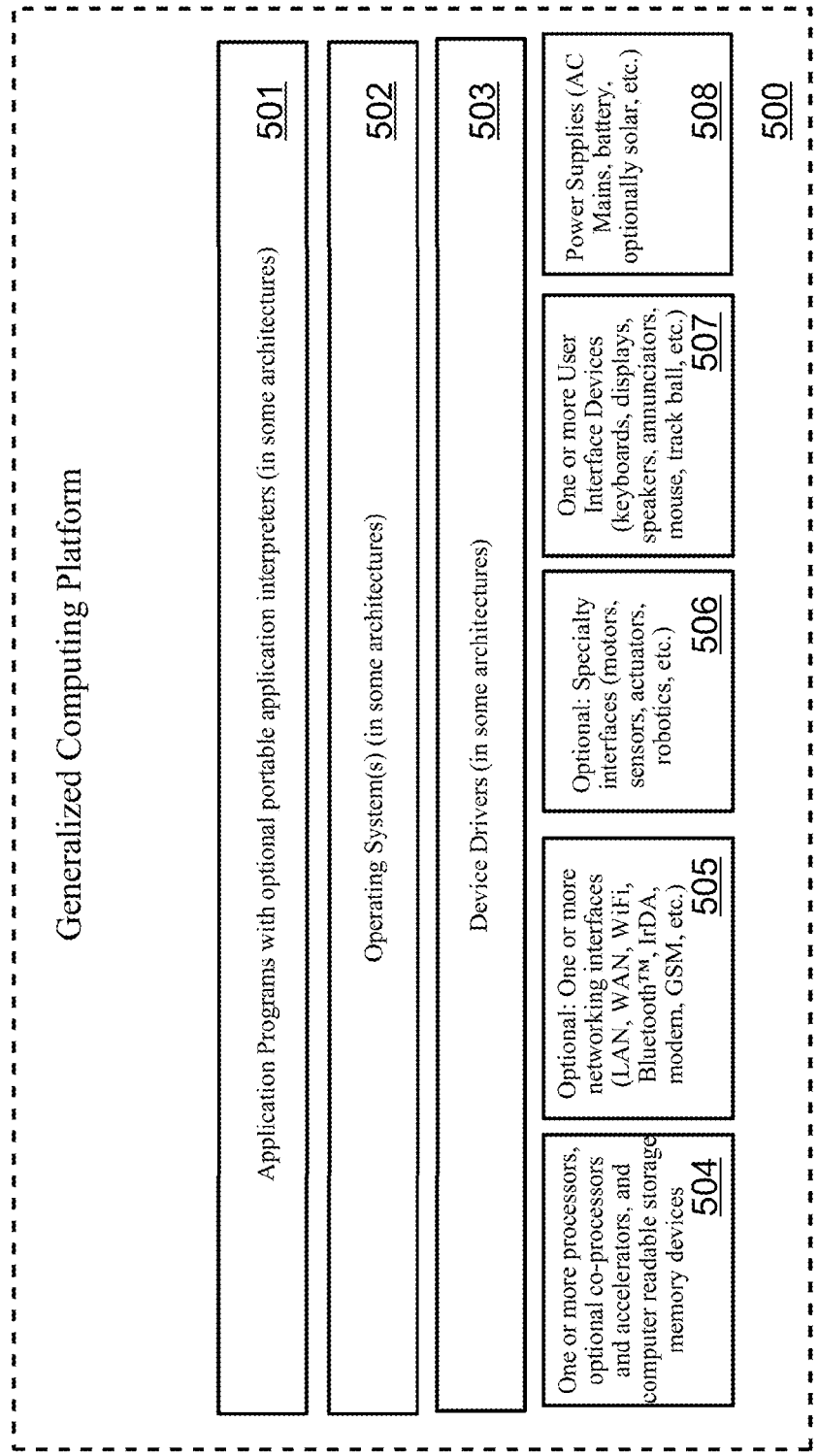
FIG. 4 sets forth a generalized perspective of common components of a computing platform, including one or more microprocessors and specialized circuitry for tangible, computer-readable memory devices and communications interfaces, as well as one or more software programs executed by the microprocessor(s).

The present and related inventions may be realized for many different processors used in many different computing platforms. FIG. 4 illustrates a generalized computing platform (500), such as common and well-known computing platforms such as "Personal Computers", web servers such as an IBM iSeries™ server, and portable devices such as personal digital assistants and smart phones, running a popular operating systems (502) such as Microsoft™ Windows™ or IBM™ AIX™, Palm OS™, Microsoft Windows Mobile™, UNIX, LINUX, Google Android™, Apple iPhone iOS™, and others, may be employed to execute one or more application programs to accomplish the computerized methods described herein. Whereas these computing platforms and operating systems are well known an openly described in any number of textbooks, websites, and public "open" specifications and recommendations, diagrams and further details of these computing systems in general (without the customized logical processes of the present invention) are readily available to those ordinarily skilled in the art.

Many such computing platforms, but not all, allow for the addition of or installation of application programs (501) which provide specific logical functionality and which allow the computing platform to be specialized in certain manners to perform certain jobs, thus rendering the computing platform into a specialized machine. In some "closed" architectures, this functionality is provided by the manufacturer and may not be modifiable by the end-user.

The "hardware" portion of a computing platform typically includes one or more processors (504) accompanied by, sometimes, specialized co-processors or accelerators, such as graphics accelerators, and by suitable computer readable memory devices (RAM, ROM, disk drives, removable memory cards, etc.). Depending on the computing platform, one or more network interfaces (505) may be provided, as well as specialty interfaces for specific applications. If the computing platform is intended to interact with human users, it is provided with one or more user interface devices (507), such as display(s), keyboards, pointing devices, speakers, etc. And, each computing platform requires one or more power supplies (battery, AC mains, solar, etc.).

CONCLUSION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof, unless specifically stated otherwise.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It should also be recognized by those skilled in the art that certain embodiments utilizing a microprocessor executing a logical process may also be realized through customized electronic circuitry performing the same logical process(es).

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A method for enhancing automated deep question and answering comprising:
   receiving by a computer from a deep question-answer computing system at least one potential answer to a user-supplied clue or user-supplied question with a confidence factor associated with each received potential answer, wherein the confidence factor comprises an estimated likelihood of correctness according to semantic analysis exclusive of a rank based on feature or keyword count;
   comparing by a computer each confidence factor to a threshold;
   responsive to a confidence factor not meeting the threshold, automatically performing by a computer a crowd sourcing operation on the user-supplied clue or user-supplied question to yield a crowd-sourced enhancement to the clue or question;
   supplying by a computer the crowd-sourced enhancement to the deep question-answer computing system;
   responsive to receiving by a computer an enhanced potential answer and associated enhanced confidence factor from the deep question-answer computing system, repeating the comparing; and
   responsive to an enhanced potential answer and associated enhanced confidence factor meeting the threshold, providing to a user the enhanced potential answer via a user interface portion of a computer system.

2. The method as set forth in claim 1 wherein the providing to a user the enhanced potential answer further comprises providing to a user the enhanced confidence factor.

3. The method as set forth in claim 1 wherein the automatically performing a crowd sourcing operation comprises performing a historical analysis of similar questions, clues or combination of questions and clues to determine potentially missing information from the received question or received clue, and performing an action to collect the missing information, and wherein the supplying a crowd-sourced enhancement to the deep question-answer computing system comprises including the collected missing information with the a crowd-sourced enhancement.

4. The method as set forth in claim 3 wherein the collection of missing information comprises prompting a user via a user interface for the missing information.

5. The method as set forth in claim 3 wherein the collection of missing information comprises retrieving the missing information from a data repository.

6. The method as set forth in claim 3 wherein the collection of missing information comprises querying one or more domain expert users via communications devices for the missing information, wherein the queried domain expert users are selected from a list of subject domain experts.

7. The method as set forth in claim 6 wherein the queried users comprise one or more users selected from the group consisting of medical doctors, medical experts, medical specialists, nurses, pharmacists, medical records specialists, family members of a patient, and caregivers of a patient.

8. The method as set forth in claim 1 further comprising, subsequent to the providing a user of an answer, continuing to provide additional crowd-source enhancements to the deep question-answer computing system, and responsive to a change in a confidence factor, to a potential answer, or to both a confidence factor and a potential answer, providing to the user via the user interface an updated possible answer reflecting the continued crowd-source enhancements.

9. The method as set forth in claim 8 wherein the updated possible answer comprises one or more answers selected from the group consisting of a pharmaceutical drug prescription, a therapy prescription, and a medical diagnosis.

10. The method as set forth in claim 6 further comprising providing a rating for each queried domain expert user and modifying or weighting input from each domain expert user according to a rating.

11. The method as set forth in claim 3 further comprising accessing an electronic patient profile containing one or more patient attributes selected from the group consisting of medical records, previous diagnoses, previous disease states, patient nationality, patient's occupation, to determine potentially missing information from the received question or received clue.

12. A computer program product for enhancing automated deep question and answering comprising:
   a tangible, computer-readable memory storage device;
   first program code for receiving from a deep question-answer computing system at least one potential answer to a user-supplied clue or user-supplied question with a confidence factor associated with each received potential answer, wherein the confidence factor comprises an estimated likelihood of correctness according to semantic analysis exclusive of a rank based on feature or keyword count;
   second program code for comparing each confidence factor to a threshold;
   third program code for, responsive to a confidence factor not meeting the threshold, automatically performing a crowd sourcing operation on the user-supplied clue or user-supplied question to yield a crowd-sourced enhancement to the clue or question;
   fourth program code for supplying the crowd-sourced enhancement to the deep question-answer computing system;
   fifth program code for, responsive to receiving an enhanced potential answer and associated enhanced confidence factor from the deep question-answer computing system, repeating the comparing; and
   sixth program code for, responsive to an enhanced potential answer and associated enhanced confidence factor meeting the threshold, providing to a user the enhanced potential answer via a user interface portion of a computer system;
   wherein the first, second, third, fourth, fifth and sixth program codes are stored by the tangible, computer-readable memory storage device.

13. The computer program product as set forth in claim 12 wherein the automatically performing a crowd sourcing operation comprises performing a historical analysis of similar questions, clues or combination of questions and clues to determine potentially missing information from the received question or received clue, and performing an action to collect the missing information, and wherein the supplying a crowd-sourced enhancement to the deep question-answer computing system comprises including the collected missing information with the a crowd-sourced enhancement.

14. The computer program product as set forth in claim 13 wherein the collection of missing information comprises at least one action selected from the group consisting of prompting a user via a user interface for the missing information, retrieving the missing information from a data repository, and querying one or more domain expert users via communications devices for the missing information, wherein the queried domain expert users are selected from a list of subject domain experts.

15. The computer program product as set forth in claim 14 wherein the queried users comprise one or more users selected from the group consisting of medical doctors, medical experts, medical specialists, nurses, pharmacists, medical records specialists, family members of a patient, and caregivers of a patient.

16. The computer program product as set forth in claim 12 wherein the supplying a crowd-sourced enhancement further comprises accessing an electronic patient profile containing one or more patient attributes selected from the group consisting of medical records, previous diagnoses, previous disease states, patient nationality, patient's occupation, to determine potentially missing information from the received question or received clue.

17. A system for enhancing automated deep question and answering comprising:
  an input portion of a computer for receiving from a deep question-answer computing system at least one potential answer to a user-supplied clue or user-supplied question with a confidence factor associated with each received potential answer, wherein the confidence factor comprises an estimated likelihood of correctness according to semantic analysis exclusive of a rank based on feature or keyword count;
  a comparator portion of a computer for comparing each confidence factor to a threshold;
  a crowd source operation trigger portion of a computer for, responsive to a confidence factor not meeting the threshold, automatically performing a crowd sourcing operation on the user-supplied clue or user-supplied question to yield a crowd-sourced enhancement to the clue or question;
  an output portion of a computer for supplying the crowd-sourced enhancement to the deep question-answer computing system;
  a controller portion of a computer for, responsive to receiving an enhanced potential answer and associated enhanced confidence factor from the deep question-answer computing system, causing the repeating the comparing and, responsive to an enhanced potential answer and associated enhanced confidence factor meeting the threshold, providing to a user the enhanced potential answer via a user interface portion of a computer system.

18. The system as set forth in claim 17 wherein the automatically performing a crowd sourcing operation comprises performing a historical analysis of similar questions, clues or combination of questions and clues to determine potentially missing information from the received question or received clue, and performing an action to collect the missing information, and wherein the supplying a crowd-sourced enhancement to the deep question-answer computing system comprises including the collected missing information with the a crowd-sourced enhancement.

19. The system as set forth in claim 18 wherein the collection of missing information comprises an action selected from the group consisting of prompting a user via a user interface for the missing information, retrieving the missing information from a data repository, and querying one or more domain expert users via communications devices for the missing information, wherein the queried domain expert users are selected from a list of subject domain experts.

20. The system as set forth in claim 17 wherein the supplying a crowd-sourced enhancement further comprises accessing an electronic patient profile containing one or more patient attributes selected from the group consisting of medical records, previous diagnoses, previous disease states, patient nationality, patient's occupation, to determine potentially missing information from the received question or received clue.

* * * * *